(12) United States Patent
Boettcher et al.

(10) Patent No.: US 7,329,749 B2
(45) Date of Patent: Feb. 12, 2008

(54) PIPERAZINYLCARBONYLQUINOLINES AND -ISOQUINOLINES

(75) Inventors: Henning Boettcher, Darmstadt (DE); Gerd Bartoszyk, Weiterstadt (DE); Juergen Harting, Darmstadt (DE); Christoph van Amsterdam, Darmstadt (DE); Christoph Seyfried, Seeheim-Jugenheim (DE)

(73) Assignee: Merck Patent Gesellschaft, Darmstadt (DE)

( * ) Notice: Subject to any disclaimer, the term of this patent is extended or adjusted under 35 U.S.C. 154(b) by 431 days.

(21) Appl. No.: 10/466,487

(22) PCT Filed: Dec. 24, 2001

(86) PCT No.: PCT/EP01/15311

§ 371 (c)(1),
(2), (4) Date: Jul. 17, 2003

(87) PCT Pub. No.: WO02/057256

PCT Pub. Date: Jul. 25, 2002

(65) Prior Publication Data

US 2004/0077657 A1  Apr. 22, 2004

(30) Foreign Application Priority Data

Jan. 17, 2001 (DE) ................. 101 02 053

(51) Int. Cl.
*A61K 31/496* (2006.01)
*C07D 403/06* (2006.01)

(52) U.S. Cl. ............ 544/373; 544/238; 544/284; 544/295; 544/296; 544/360; 544/363; 544/367; 544/368; 544/369; 544/370; 544/371; 544/233; 514/254.09

(58) Field of Classification Search ........... 544/238, 544/284, 295, 296, 360, 363, 367, 368, 369, 544/370, 371, 373, 233; 514/254.09
See application file for complete search history.

(56) References Cited

U.S. PATENT DOCUMENTS 6,838,461 B1 * 1/2005 Boettcher et al. ...... 514/254.09

FOREIGN PATENT DOCUMENTS

EP   0957100   11/1999

EP   0957100 A1 * 11/1999

OTHER PUBLICATIONS

Ismaiel et al., "Ketanserin Analogues . . . ", J. Med. Chem. 1995, 38, 1196-1202.*
Kehne et al., "Preclinical Characterization . . . ", J. Pharm & Experimental Therapetuics, Vo. 277, No. 2, 1996.*
Younes et al., "Synthesis and structure . . . ", Eur. J. Med. Chem 35 (2000) 107-121.*
Padich et al., "5-HT modulation of auditory and visual sensorimotor gating: II. Effects of the 5-HT$_{2A}$ antagonist MDL 100,907 on disruption of sound and light prepulse inhibition produced by 5-HT agaonists in Wistar rats", Psychopharmacology (1996) 124: pp. 107-116.
Carlsson et al., "The 5-HT2A receptor antagonist M100907 is more effective in counteracting NMDA antagonist- than dopamine agonist-induced hyperactivity in mice", J Neural Transm (1999) 106: pp. 123-129.
Hanson et al., "Comparison of Neurotensin Responses to MDL 100,907, a Selective 5HT$_{2A}$ Antagonist, with Clozapine and Haloperidol", Brain Research Bulletin, vol. 42, No. 3, pp. 211-219, 1997.
S.Younes et al ; "Synthesis and Structure—Activity Relationship of Novel Aryalkyl 4-Benzyl Piperazine Derivatives as Sigma Site Selective Ligands" Eur. J. Med. Chem. vol. 35, Jan. 2000, pp. 107-121 XP004330406.
Ismaiel A M et al: "Ketanserin Analogues: the Effect of Structural Modification on 5-HT2 Serotonin Receptor Binding" Journel of Medicinal Chemistry, Amercian Chemical Society. Washington, US, vol. 38, No. 7, 1995, pp. 1196-1202, XP002166697.
Kehne J H et al: "Preclinical Characterization of the Potential of the Putative Atypical Antipsychotic MDL 100,907 as a Potent 5-HT 2A Antogonist with a Favorable CNS Safety Profile" Journal of Pharmacology and, US vol. 277, No. 2, May 1996, pp. 968-981, XP000904752.

* cited by examiner

*Primary Examiner*—James O. Wilson
*Assistant Examiner*—Paul V. Ward
(74) *Attorney, Agent, or Firm*—Millen, White, Zelano & Branigan, P.C.

(57) ABSTRACT

Compound of the formula (I) in which $R^1$, $R^2$ and alk are as defined in Claim 1, are potent 5-HT$_{2A}$ antagonist and are suitable for the treatment of psychoses, schizophrenia, depression, neurological disorders, memory disorders, Parkinson's disease, amyotrophic lateral sclerosis, Alzheimer's disease, Hutington's disease, eating disorders, such as bulimia, anorexia nervosa, premenstrual syndrome and/or for positively influencing obsessive-compulsive disorder (OCD).

16 Claims, No Drawings

PIPERAZINYLCARBONYLQUINOLINES AND -ISOQUINOLINES

FIELD OF THE INVENTION

The present invention relates to Glucocerebrosidase (GCR) bifunctional fusion proteins (GCR fusion proteins) consisting essentially of an Immunoglobulin (Ig) molecule (whole antibody, an Ig heavy or light chain or a fragment thereof) and a protein (the term includes also oligopeptides) having the biological activity of GCR (GCR-like protein), for enzyme replacement therapy and/or augmentation of glycolipid metabolism by the administration of bifunctional fusion proteins using a therapy based on the treatment of glycolipid storage disorders such as Gaucher's, Fabry's and Tay-Sachs diseases.

By selective altering of the amino acid sequences of the Ig moiety, GCR fusion proteins with improved properties, e.g. enhanced stability, can be obtained. Furthermore, fusion proteins can be provided, wherein shortened versions of GCR and the Ig chain are used.

The present invention relates also to pharmaceutical compositions and therapeutic methods and systems comprising such GCR fusion proteins and methods of treating Gaucher's disease or another disease caused by glycolipid storage disorders, such as Fabry's and Tay-Sachs disease, comprising administering to a subject afflicted with this disease, a pharmaceutical composition comprising a therapeutic amount of recombinantly produced GCR fusion protein in a pharmaceutically acceptable carrier.

BACKGROUND

The administration of exogenous β-glucosidase to treat diseases caused by glycolipid storage disorders like Gaucher's, Tay-Sachs' or Fabry's disease as attempts of enzyme augmentation in an organism suffering from such a disease It has been found that the compounds of the formula I and their physiologically acceptable salts and solvates are well tolerated and have valuable pharmacological properties since they have actions on the central nervous system. Surprisingly, the compounds have selective affinity to 5-$HT_{2A}$ receptors. In particular, they are selective 5-$HT_{2A}$ antagonists.

The substances specified in this application are selective 5-$HT_{2A}$ antagonists. 5-$HT_{2A}$ antagonists exhibit clinically antipsychotic activity with no or with minimal side effects. Accordingly, the substances of this application are to be regarded as antipsychotics having few side effects. They can in addition be used in the treatment of neurological illnesses attributable to disturbances in serotonergic transmission, such as depresssion, anxiety states, panic attacks, obsessive-compulsive disorders, pain, sleep disturbances, sleeplessness, eating disorders, such as anorexia nervosa, bulimia, addictive behaviour, dependence on certain addiction-causing substances, such as LSD and MDMA, cardiovascular disorders, such as various angina illnesses, Reynaud's syndrome, intermittent claudication, cardiac or peripheral vascular spasms, fibromyalgia, cardiac arrhythmia and thrombotic illnesses, since the substances inhibit blood plate-let aggregation. In combination with classical or atypical neuroleptics, the side effects can be suppressed. Owing to the reduction in ocular pressure, the substances can also be employed in glaucoma therapy. Toxic symptoms caused by poisoning with, for example, ergovalin can be suppressed using the substances.

For in-vitro detection of the affinity to 5-$HT_{2A}$ receptors, the following test (Example A1), for example, can be used. The 5-$HT_{2A}$ receptors are exposed both to [$^3$H]ketanserine (a substance which is known for its affinity to the receptor) and also to the test compound. The decrease in the affinity of [$^3$H]ketanserine to the receptor is an indication of the affinity of the test substance to the 5-$HT_{2A}$ receptor. The detection is carried out analogously to the description by J. E. Leysen et al., Molecular Pharmacology, 1982, 21: 301-314, or as also described, for example, in EP 0320983.

The effectiveness of the compounds according to the invention as 5-$HT_{2A}$ receptor antagonists can be measured in vitro analogously to W. Feniuk et al., Mechanisms of 5-hydroxytryptamine-induced vasoconstriction, in: The Peripheral Actions of 5-Hydroxytryptamine, ed. Fozard J. R., Oxford University Press, New York, 1989, p. 110. Thus, the contractility of-the rat tail artery caused by 5-hydroxytryptamine is mediated by 5-$HT_{2A}$ receptors. For the test system, vessel rings prepared from the ventral rat tail artery are subjected to perfusion in an organ bath containing an oxygen-saturated solution. By introducing increasing concentrations of 5-hydroxytryptamine into the solution, a response is obtained to the cumulative concentration of 5-HT. The test compound is then added to the organ bath in suitable concentrations, and a second concentration curve for 5-HT is measured. The strength of the test compound in shifting the 5-HT-induced concentration curve to higher 5-HT concentrations is a measure of the 5-$HT_{2A}$ receptor antagonistic property in vitro.

The 5-$HT_{2A}$-antagonistic property can be determined in vivo analogously to M. D. Serdar et al., Psychopharmacology, 1996, 128: 198-205.

Other compounds which likewise exhibit 5-$HT_2$antagonistic actions are described, for example, in EP 0320983.

Similar piperazine derivatives having antiarrhythmic properties are disclosed, for example, in EP 0431944 and EP 0431945.

5-Isoquinolinesulfonamides are described by A. Morikawa et al. in Chem. Pharm. Bull. 1992, 40, 770-3, or in EP 61673 as vasodilators.

M. Ohashi et al. in JP 631761177 describe piperazinesulfonyl derivatives as decolourising ag nts.

Selective antagonists at the 5-$HT_{2A}$ receptor can preferably be employed against 5-$HT_2$ receptor antagonists. This is because 5-$HT_2$ receptor antagonists also bind to other receptor sub-types of the 5-$HT_2$ group, such as, for example, to the 5-$HT_{2C}$ receptor. It is now being discussed that a 5-$HT_{2C}$ receptor antagonism may cause undesired weight gain (E. Richelson and T. Souder, Life Sci. 2000, 68, 29-39). Selective 5-$HT_{2A}$ receptor antagonists do not induce this effect.

The compounds of the formula I are suitable both in veterinary and in human medicine for the treatment of disturbances in the function of the central nervous system and of inflammations. They can be used for the prophylaxis and combating of the consequences of cerebral infarction phenomena (apoplexia cerebri), such as strokes and cerebral ischemia, and for the treatment of extrapyramidal motor and psychic side effects of neuroleptics and of Parkinson's disease, for the treatment of Parkinson's disease in general, for the acute and symptomatic therapy of Alzheimer's disease and for the treatment of amyotrophic lateral sclerosis. They are likewise suitable as therapeutic agents for the treatment of brain and spinal traumas. In particular, however, they are suitable as medicament active ingredients for anxiolytics, antidepressants, antipsychotics, neuroleptics, antihypertonics and/or for positively influencing obsessive-compulsive disorder (OCD), anxiety states and physiological changes associated with anxiety states, such as, for example, tachycardia, tremor or sweating, panic attacks, psychoses, schizophrenia, inclusive schizotypical personality disorders, for the prevention of schizophrenia in first degree relatives and treatment-resistant schizophrenia, anorexia, delusional obsessions, agoraphobia, migraines, cognitive deficits, Alzheimer's disease and other forms of dementia, for example vascular dementia, Lewy body dementia and dementia in Parkinson's disease, behaviour disturbances in dementia, in particular in the elderly, sleep disturbances, including sleep apnoea, tardive dyskinesia and of psychoses in tardive dyskinesia, learning disorders, age-dependent memory disorders, attention deficit disorders with hyperactivity and behaviour disorders, eating disorders, such as bulimia, drugs misuse, such as, for example, of alcohol, opiates, nicotine, psychostimulants, such as, for example, cocaine or amphetamines, disturbances of sexual function, aggression disorders in youths and adults, conditions of pain of all types and fibromyalgia.

The compounds of the formula I are suitable for the treatment of extrapyramidal side effects (EPS) of neuroleptics. EPS are characterised by Parkinson's-like syndromes, acathisia and dystonic reactions (for example described in EP 337136 for 5-$HT_2$ antagonists).

They are furthermore suitable for the treatment of anorexia nervosa, angina, Reynaud's phenomenon, coronary vasospasms, in the prophylaxis of migraines (for example described in EP 208235 for 5-$HT_2$ antagonists), pain and neuralgia (for example described in EP 320983 for 5-$HT_2$ antagonists), for the treatment of Rett syndrome with autistic traits, of Asperger syndrome, of autism and autistic disorders, in concentration deficit states, development disorders, hyperactivity states with mental underdevelopment and stereotypical behaviour states (for example described in WO 9524194 for 5-$HT_2$ antagonists).

The compounds according to the invention are particularly suitable for the treatment of schizophrenia.

They are furthermore suitable for the treatment of endocrine illnesses, such as hyperprolactinemia, furthermore in vasospasms, thrombotic illnesses (for example described in WO 9946245 for 5-$HT_2$ antagonists), hyper-tension and gastrointestinal illnesses.

They are furthermore suitable for the treatment of cardiovascular illnesses and extrapyramidal symptoms, as described in WO 99/11641, on page 2, lines 24-30, for 5-$HT_2$ antagonists.

They can furthermore be employed as intermediates in the preparation of further medicament active ingredients.

The invention relates to the piperazinylcarbonylquinolines and -isoquino-lines of the formula I and to their physiologically acceptable acid-addition salts. The invention also relates to the solvates, for example hydrates or alcoholates, of these compounds.

The term solvates of the compounds of the formula I is taken to mean adductions of inert solvent molecules onto the compounds of the formula I which form owing to their mutual attractive force. Solvates are, for example, mono- or dihydrates or addition compounds with alcohols, such as, for example, with methanol or ethanol.

The invention relates to the compounds of the formula I and their salts and solvates according to Claim 1 and to a process for the preparation of compounds of the formula I and their salts and solvates, characterised in that a) a compound of the formula II

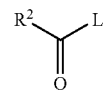

in which L is Cl, Br, I or a free or reactively functionally modified OH group, and $R^2$ is as defined in Claim 1, is reacted with a compound of the formula III

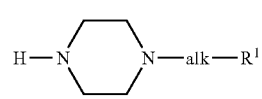

in which $R^1$ and alk are as defined in Claim 1, or b) a compound of the formula IV

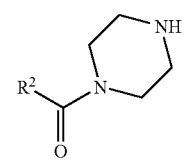

in which $R^2$ is as defined in Claim 1, is reacted with a compound of the formula V L-alk-$R^1$   V in which L is Cl, Br, I or a free or reactively functionally modified OH group, and $R^1$ and alk are as defined in Claim 1, or c) if desired, one of the radicals $R^2$, $R^3$, $R^4$ and/or $R^5$ is converted into another radical $R^2$, $R^3$, $R^4$ and/or $R^5$ by, for example, cleaving an OA group to form an OH group and/or converting a CHO group into a CN group, and/or a resultant base of the formula I is converted into one of its salts by treatment with an acid.

The invention also relates to the compounds of the formula I according to Claim 1 and to their physiologically acceptable salts and solvates as medicament active ingredients.

The invention furthermore relates to the compounds of the formula I according to Claim 1 and their physiologically acceptable salts or solvates as inhibitors of the 5-$HT_{2A}$ receptor.

The invention also relates to the compounds of the formula I and their enantiomers and diastereomers and to their salts.

For all radicals which occur more than once, such as, for example, A or Hal, their meanings are independent of one another.

The radical A is alkyl and has 1 to 6, preferably 1, 2, 3 or 4, in particular 1 or 2, carbon atoms. Alkyl is therefore in particular, for example, methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore trifluoromethyl or pentafluoroethyl.

Acyl preferably has 1-6 carbon atoms and is, for example, formyl, acetyl, propionyl, butyryl, furthermore trifluoroacetyl or pentafluoropropionyl. acyl is particularly preferably acetyl alk is alkylene having 1, 2, 3, 4, 5 or 6 carbon atoms, is unbranched or branched and is preferably methylene, ethylene, propylene, butylene or pentylene. alk is very particularly preferably ethylene.

OA is preferably methoxy, trifluoromethoxy, furthermore also ethoxy, n-propoxy, isopropoxy, n-butoxy, isobutoxy, sec-butoxy or tert-butoxy.

$Het^1$ is a monocyclic or bicyclic, unsaturated heterocyclic ring system having from 5 to 10 ring members which is unsubstituted or monosubstituted or disubstituted by Hal, A, OA or OH and which contains one, two or three identical or different hetero atoms, such as nitrogen, oxygen and sulfur $Het^1$ is preferably 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 5-pyridazinyl, pyrazinyl, 2,-, 3-, 4-, 5- 6- or 7-benzo-furyl, 2-, 3-, 4-, 5:-, 6- or 7-benzothienyl, 1-, 2-, 3-, 4-, 5-, 6- or 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolyl, or 2-, 4-, 5-, 6-, 7- or 8-quinazo-linyl.

Hal is fluorine, chlorine, bromine or iodine, in particular fluorine or chlorine. Hal is very particularly preferably fluorine.

$R^1$ is a phenyl or naphthyl radical, each of which is unsubstituted or substituted by $R^3$ and/or $R^4$, or $Het^1$, where $Het^1$ has one of the meanings mentioned above, and $R^3$ and $R^4$ have one of the meanings mentioned below.

$R^1$ is preferably unsubstituted or monosubstituted phenyl or naphthyl, in detail preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-hydroxyphenyl, o-, m- or p-nitrophenyl, o-, m- or p-(trifluoromethoxy)phenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-(difluoromethoxy)phenyl, o-, m- or p- (fluoromethoxy)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl4-chlorophenyl, 2-bromo-3-methyl-, 2-bromo4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,4- or 3,4-dimethoxyphenyl, 3-nitro4-chlorophenyl, 2,3,4-, 2,3,5-, 2,3,6-, 2,4,6- or 3,4,5-trichlorophenyl, 2,4,6-tri-tert-butylphenyl, furthermore preferably 2-nitro4-(trifluoromethyl)-phenyl, 3,5-di(trifluoromethyl)phenyl, 2,4-dimethylphenyl, 2-hydroxy-3,5-dichlorophenyl, 2-fluoro-5- or 4-fluoro-3-(trifluoromethyl) phenyl, 4-chloro-2- or 4-chloro-3-(trifluoromethyl)-, 2-chloro-4- or 2-chloro-5-(trifluoromethyl)-phenyl, 4-bromo-2- or 4-bromo-3-(trifluoromethyl)phenyl, p-iodophenyl, 2-nitro-4-methoxyphenyl, 2,5-dimethoxy4-nitrophenyl, 2-methyl-5-nitro-phenyl, 2,4-dimethyl-3-nitrophenyl, 4-fluoro-3-chlorophenyl, 4-fluoro-3,5-dimethylphenyl, 2-fluoro4-bromophenyl, 2,5-difluoro-4-bromophenyl, 2,4-dichloro-5-methylphenyl, 3-bromo-6-methoxyphenyl, 3-chloro-6-methoxy-phenyl, 2-methoxy-5-methylphenyl or 2,4,6-triisopropylphenyl. $R^1$ is very particularly preferably 4-fluorophenyl.

$R^2$ is a quinolinyl or isoquinolinyl radical which is unsubstituted or substituted by $R^5$ and/or $R^6$, where $R^5$ and $R^6$ may have one of the above-mentioned meanings, and the linking of the quinolinyl radical can take place in the 2-, 3-, 4-, 5-, 6-, 7- or 8-position and the linking of the isoquinolinyl radical can take place in the 1-, 3-, 4-, 5-, 6-, 7- or 8-position. $R^2$ is particularly preferably isoquinolin-1-yl, isoquinolin-3-yl, quinolin-2-yl or quinolin-8-yl.

$R^3$ and $R^4$ are each, independently of one another, preferably H, Hal, alkyl having 1-6 carbon atoms, alkoxy having 1-6 carbon atoms or hydroxyl, furthermore cyano or acyl.

$R^3$ is preferably H, Hal, A, OA, OH, CN or acyl. $R^4$ is preferably H. $R^3$ is very particularly preferably Hal.

$R^5$ and $R^6$ are each, independently of one another, preferably H, CN, acyl, Hal, A, OA, OH, $CONH_2$, CONHA or $CONA_2$, where A and acyl have one of the meanings indicated above. $R^5$ is preferably H. $R^6$ is preferably H.

Accordingly, the invention relates in particular to the compounds of the formula I in which at least one of the said radicals has one of the preferred meanings indicated above. Some preferred groups of compounds may be expressed by the following sub-formulae Ia to Ie which correspond to the formula I and in which the radicals not denoted more precisely are as defined for the formula I, but in which in Ia $R^1$ is a phenyl radical which is unsubstituted or substituted by $R^3$ and/or $R^4$;

in Ib alk is ethylene;

in Ic $R^1$ is a phenyl radical which is unsubstituted or substituted by $R^3$ and/or $R^4$, and alk is ethylene;

in Id $R^3$ is Hal and $R^4$ is H;

in Ie $R^1$ is a phenyl radical which is unsubstituted or substituted by $R^3$ and/or $R^4$, alk is ethylene, $R^3$ is Hal and $R^4$ is H.

The compounds of the formula I and also the starting materials for their preparation are, in addition, prepared by methods known per se, as described in the literature (for example in standard works such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the formula I. On the other hand, it is possible to carry out the reaction stepwise.

In the compounds of the formulae II and V, the radical L is preferably Cl or Br; however, it may also be I, OH or also preferably a reactively functionally modified OH group, in particular alkylsulfonyloxy having 1-6 carbon atoms (for example methanesulfonyloxy) or arylsulfonyloxy having 6-10 carbon atoms (for example benzenesulfonyloxy, p-toluenesulfonyloxy, 1- or 2-naphthalenesulfonyloxy) or alternatively trichloromethoxy, alkoxy, such as, for example, methoxy, ethoxy, propoxy or butoxy, furthermore also phenoxy.

The compounds of the formula I can preferably be obtained by reacting compounds of the formula II with compounds of the formula III.

The starting materials of the formulae II and III are generally known; the compounds of the formulae II and III which are not known can readily be prepared analogously to the known compounds.

The reaction of the compounds II and III proceeds by methods as are known from the literature for the alkylation or acylation of amines. However, it is also possible to react the compounds in the presence of an inert solvent. Examples of suitable solvents are hydrocarbons, such as benzene, toluene or xylene; ketones, such as acetone or butanone; alcohols, such as methanol, ethanol, isopropanol or n-butanol; ethers, such as tetrahydrofuran (THF) or dioxane; amides, such as dimethylformamide (DMF) or N-methylpyrrolidone; nitriles, such as acetonitrile, if desired also mixtures of these solvents with one another or mixtures with water. The addition of an acid-binding agent, for example an alkali or alkaline earth metal hydroxide, carbonate or bicarbonate or of another salt of a weak acid of the alkali metals or alkaline earth metals, preferably of potassium, sodium or calcium, or the addition of an organic base, such as triethylamine, dimethyl-aniline, pyridine or quinoline, or of an excess of piperazine derivative of the formula II, may be favourable. Depending on the conditions used, the reaction time is between a few minutes and 14 days, and the reaction temperature is between about 0 and 150°, normally between 20 and 130°.

Furthermore, compounds of the formula I can be prepared by reacting amines of the formula IV with a component of the formula V containing the radical $R^1$.

The respective components are generally known or can be prepared by known processes as already described.

A resultant base of the formula I can be converted into the associated acid-addition salt using an acid. Suitable acids for this reaction ar those which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid or sulfamic acid, furthermore organic acids, in detail aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

The free bases of the formula I may, if desired, be liberated from their salts by treatment with strong bases, such as sodium hydroxide, potassium hydroxide, sodium carbonate or potassium carbonate, so long as the molecule contains no further acidic groups. In those cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

The invention furthermore relates to the medicaments according to the invention having a $5\text{-HT}_{2A}$ receptor antagonistic action for the treatment of psychoses, schizophrenia, depression, neurological disorders, memory disorders, Parkinson's disease, amyotrophic lateral sclerosis, Alzheimers disease, Huntington's disease, eating disorders, such as bulimia, anorexia nervosa, premenstrual syndrome and/or for positively influencing obsessive-compulsive disorder (OCD).

The invention furthermore relates to pharmaceutical preparations prepared, in particular, by non-chemical methods which comprise at least one compound of the formula I and/or one of its physiologically acceptable salts or solvates and at least one pharmaceutically acceptable assistant. The compounds of the formula I here can be converted into a suitable dosage form together with at least one solid, liquid and/or semi-liquid excipient or assistant and if desired in combination with one or more further active ingredient(s).

These preparations can be employed as medicaments in human and veterinary medicine. Suitable excipients are organic or inorganic substances which are suitable for enteral (for example oral), parenteral or topical application and do not react with the novel compounds, for example water, vegetable oils, benzyl alcohols, polyethylene glycols, glycerol triacetate, gelatine, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral application are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The preparations indicated may be sterilised and/or comprise auxiliaries, such as lubricants, preservatives, stabilisers and/or wetting agents, emulsifiers, salts for modifying the osmotic pressure, buffer substances, dyes, flavours and/or a plurality of further active ingredients, for example one or more vitamins.

The substances according to the invention are generally administered analogously to known preparations, preferably in doses of between about 0.1 and 500 mg, in particular between 5 and 300 mg, per dosage unit. The daily dose is preferably between about 0.01 and 250 mg/kg, in particular between 0.02 and 100 mg/kg of body weight.

However, the specific dose for each particular patient depends on an extremely wide variety of factors, for example on the efficacy of the specific compound employed, on the age, body weight, general state of health, sex, on the diet, on the time and method of administration, on the rate of excretion, medicament combination and severity of the particular illness to which the therapy applies. Oral administration is preferred.

The invention furthermore relates to the use of the compounds according to the invention and/or of their physiologically acceptable salts and solvates for the preparation of a medicament, in particular a medicament having a $5\text{-HT}_{2A}$ receptor antagonistic action.

The invention also relates to the use of the compounds according to the invention and/or their physiologically acceptable salts and solvates for the preparation of a medicament having a 5-HT$_{2A}$ receptor antagonistic action for the treatment of schizophrenia.

The invention also relates to the use of the compounds according to the invention and/or of their physiologically acceptable salts and solvates for the preparation of a medicament having a 5-HT$_{2A}$ receptor antagonistic action for the treatment of psychoses, depression, neurological disorders, memory disorders, Parkinson's disease, amyotrophic lateral sclerosis, Alzheimer's disease, Huntington's disease, eating disorders, such as bulimia, anorexia nervosa, premenstrual syndrome and/or for positively influencing obsessive-compulsive disorder (OCD).

The invention furthermore relates to selective 5-HT$_{2A}$ receptor antagonists for the treatment of psychoses, schizophrenia, depression, neurological disorders, memory disorders, Parkinson's disease, amyotrophic lateral sclerosis, Alzheimer's disease, Huntington's disease, eating disorders, such as bulimia, anorexia nervosa, premenstrual syndrome and/or for positively influencing obsessive-compulsive disorder (OCD).

The invention furthermore relates to selective 5-HT$_{2A}$ receptor antagonists for the treatment of psychoses, schizophrenia, depression, neurological disorders, memory disorders, Parkinson's disease, amyotrophic lateral sclerosis, Alzheimer's disease, Huntington's disease, eating disorders, such as bulimia, anorexia nervosa, premenstrual syndrome and/or for positively influencing obsessive-compulsive disorder (OCD), characterised in that the antagonists do not bind to other relevant receptors. Whereas the IC$_{50}$ at the 5-HT$_{2A}$ receptor is 1 nM, for example, for the substance described in Example 1, it is greater than 1 μM for the 5-HT$_{2C}$ receptor, the 5-HT$_{1A}$ receptor, the 5-HT$_{1B}$ receptor, the 5-HT$_{1D}$ receptor and the D$_2$ receptor, i.e. the affinities differ by a factor of greater than 1000. In the substance class described, selectivities with respect to other G-protein-coupled receptors of from 10 to more than 1000 are found.

The invention likewise relates to the use of a selective 5-HT$_{2A}$ antagonist for the preparation of a medicament for the treatment of schizophrenia.

The invention also relates to the use of a selective 5-HT$_{2A}$ antagonist for the preparation of a medicament for the treatment of psychoses, depresssion, neurological disorders, memory disorders, Parkinson's disease, amyotrophic lateral sclerosis, Alzheimer's disease, Huntington's disease, eating disorders, such as bulimia, anorexia nervosa, premenstrual syndrome and/or for positively influencing obsessive-compulsive disorder (OCD).

Above and below, all temperatures are given in ° C. In the examples below, "conventional work-up" means that the solvent is removed if necessary, water is added if necessary, the mixture is adjusted, if necessary, to a pH of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. The purified compounds are, if desired, freeze-dried.

EXAMPLE A1

Preparation of a suspension of 5-HT$_{2A}$ receptors: Frontal rat cortex is homogenised in ice-cold buffer. The homogenate is centrifuged at 4° C. and 50,000×for 10 minutes. The pellet is re-suspended in 2.5 ml of ice-cold tris buffer, made up with 10 ml of additional buffer and centrifuged as described. The pellet is then re-suspended in buffer and diluted to give a homogenate which comprises 60 mg of material/ml. 0.1 ml of the suspension, 100 μl of a 5 nM solution of [$^3$H]ketanserine, 100 μl of a solution of the test compound (concentration in the range from 10$^{-5}$ to 10$^{-10}$ mol per litre) are introduced into the incubation tubes and made up to 1 ml with buffer. The tubes are incubated at 37° C. for 15 minutes. After the incubation has been interrupted by immersing the tubes into an ice bath, the cooled suspension is filtered through a glass filter under reduced pressure. The filters are washed 3× with 5 ml of cold buffer and then transferred into scintillation tubes. The filters are analysed by liquid scintillation spectrometry in 8 ml of Triton-X scintillator liquid.

Example 1

0.9 g of 1,1'-carbonyldiimidazole is added to a solution of 1 g of isoquinoline-1-carboxylic acid in 100 ml of tetrahydrofuran (THF), and the mixture is stirred at room temperature for 2 hours. 1.6 g of 1-[2-(4-fluorophenyl)ethyl]piperazine and 2.4 ml of triethylamine are added to this mixture, which is stirred for a further 80 hours. ConventionaL work-up gives {4-[2-(4-fluorophenyl)ethyl]piperazin-1-yl}isoquinolin-1-ylmethanone.

For salt formation, 1N hydrochloric acid is added to a solution of {4-[2-(4-fluorophenyl)ethyl]piperazin-1-yl}isoquinolin-1-ylmethanone in 60 ml of acetone and 50 ml of ether until crystals form. When crystallisation is complete, the mother liquor is filtered off, and the precipitate is washed with ether and dried, giving {4-[2-(4-fluorophenyl)ethyl]piperazin-1-yl}isoquinolin-1-ylmethanone, hydrochloride, m.p. 238-240°.

Example 2

Analogously to Example 1, quinaldic acid is reacted with 1-[2-(4-fluoro-phenyl)ethyl]piperazine, giving {4-[2-(4-fluorophenyl)ethyl]piperazin-1-yl}-quinolin-2-ylmethanone.

Crystallisation using 1N hydrochloric acid analogously to Example 1 gives {4-[2-(4-fluorophenyl)ethyl]piperazin-1-yl}quinolin-2-ylmethanone, hydrochloride; m.p. 221-222°.

Example 3

0.34 ml of thionyl chloride is added to a suspension of 0.4 g of quinoline-8-carboxylic acid in THF, and the mixture is refluxed for 1 hour. The mixture is then freed from solvent, and the residue (quinoline-8-carbonyl chloride) is taken up in 50 ml of dichloromethane. 2.1 g of polymeric DMAP (Aldrich, Article No. 35,998-2), 0.6 ml of triethylamine and 0.6 g of 1-[2-(4-fluoro-phenyl)ethyl]piperazine are added to this solution, and the mixture is stirred at room temperature for 5 days. Conventional work-up gives {4-[2-(4-fluorophenyl)ethyl]piperazin-1-yl}quinolin-8-ylmethanone.

Salt formation by reaction of a solution of {4-[2-(4-fluorophenyl)ethyl]-piperazin-1-yl}quinolin-8-ylmethanone in 30 ml of acetone with 0.2 ml of ethanolic hydrochloric acid gives {4-[2-(4-fluorophenyl)ethyl]piperazin-1-yl}quinolin-8-ylmethanone, hydrochloride, m.p. 219-220.5°.

Example 4

Analogously to Example 3, firstly isoquinoline-3-carboxylic acid is reacted with thionyl chloride, and the resultant isoquinoline-3-carbonyl chloride is reacted with 1-[2-

(4-fluorophenyl)ethyl]piperazine, giving {4-[2-(4-fluorophenyl)ethyl]piperazin-1-yl}isoquinolin-3-ylmethanone.

Salt formation analogously to Example 3 gives amorphous {4-[2-(4-fluoro-phenyl)ethyl]piperazin-1-yl}isoquinolin-3-ylmethanone, hydrochloride, m.p. 163-170°.

The examples below relate to pharmaceutical preparations:

Example A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised and sealed under sterile conditions. Each injection vial contains 5 mg of active ingredient.

Example B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

Example C

Solution

A solution is prepared from 1 g of an active ingredient of the formula I, 9.38 g of $NaH_2PO_4 \times 2\ H_2O$, 28.48 g of $Na_2HPO_4 \times 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F

Coated Tablets

Tablets are pressed analogously to Example E and subsequently coated in a conventional manner with a coating of sucrose, potato starch, talc, traga-canth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is transferred into ampoules, lyophilised under aseptic conditions and sealed under sterile conditions. Each ampoule contains 10 mg of active ingredient.

The invention claimed is:

1. A compound of the formula I

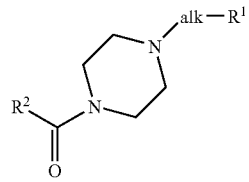

in which
  $R^1$ is a phenyl or naphthyl radical which is unsubstituted or substituted by $R^3$ and/or $R^4$, or is $Het^1$,
  $R^2$ is a quinolinyl or isoquinolinyl radical which is unsubstituted or substituted by $R^5$ and/or $R^6$,
  $R^3$ and $R^4$ are each, independently of one another, H, Hal, A, OA, OH or CN,
  $R^5$ and $R^6$ are each, independently of one another, H, CN, acyl, Hal, A, OA, OH, $CONH_2$, CONHA or $CONA_2$,
  $Het^1$ is a monocyclic or bicyclic, unsaturated heterocyclic ring system which is unsubstituted or monosubstituted or disubstituted by Hal, A, OA or OH and which contains one, two or three identical or different heteroatoms, selected from nitrogen, oxygen and sulfur,
  A is alkyl having 1-6 carbon atoms,
  alk is alkylene having 1-6 carbon atoms,
  Hal is F, Cl, Br or I,
or a physiologically acceptable salt thereof.

2. A compound of the formula I according to claim 1, wherein $R^1$ is a phenyl radical which is unsubstituted or substituted by $R^3$ and/or $R^4$.

3. A compound of the formula I according to claim 1, wherein alk is ethylene.

4. A compound of the formula I according to claim 1, wherein $R^3$ is halogen and $R^4$ is hydrogen.

5. A compound according to claim 1, selected from:
  a) {4-[2-(4-fluorophenyl)ethyl]piperazin-1-yl}isoquinolin-1-yl-methanone,
  b) {4-[2-(4-fluorophenyl)ethyl]piperazin-1-yl}quinolin-2-ylmethanone,
  c) {4-[2-(4-fluorophenyl)ethyl]piperazin-1-yl}quinolin-8-ylmethanone,
  d) {4-[2-(4-fluorophenyl)ethyl]piperazin-1-yl}isoquinolin-3-yl-methanone,
or a physiologically acceptable salt thereof.

6. A process for the preparing a compound of the formula I according to claim 1, comprising:

a) a compound of the formula II

in which L is Cl, Br, I or a free or reactively functionally modified OH group, and $R^2$ is as defined in claim 1, with a compound of the formula III

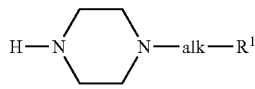

in which $R^1$ and alk are as defined in claim 1, or b) reacting a compound of the formula IV

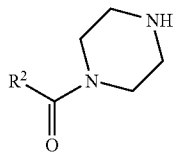

in which $R^2$ is as defined in claim 1, with a compound of the formula V

L-alk-$R^1$     V in which L is Cl, Br, I or a free or reactively functionally modified OH group, and $R^1$ and alk are as defined in claim 1, and/or c) converting one of the radicals $R^2$, $R^3$, $R^4$ and/or $R^5$ into another radical $R^2$, $R^3$, $R^4$ and/or $R^5$, and/or d) converting a resultant base of the formula I into one of its salts by treatment with an acid.

7. A compound of the formula I according to claim 2, wherein alk is ethylene.

8. A compound of the formula I according to claim 2, wherein $R^3$ is halogen and $R^4$ is hydrogen.

9. A compound of the formula I according to claim 3, wherein $R^3$ is halogen and $R^4$ is hydrogen.

10. A compound of the formula I according to claim 1, wherein $Het^1$ is 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4- 4H-thiopyranyl, 3- or 5-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazoly, 2-, 4-, 5-, 6- or 7-benzisothiazolyl, 4-, 5-, 6- or 7-benz-9 1 oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolyl, or 2-, 4-, 5-, 6-, 7- or 8-quinazlinyl.

11. A compound of the formula I according to claim 1, wherein alk is alkylene having 3-6 carbon atoms.

12. A compound of the formula I according to claim 1, wherein alk is alkylene having 4-6 carbon atoms.

13. A compound of the formula I

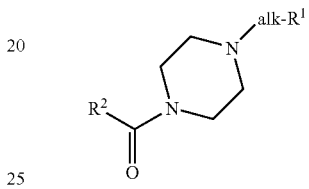

in which $R^1$ is a phenyl or naphthyl radical which is unsubstituted or substituted by $R^3$ and/or $R^4$, or is $Het^1$, $R^2$ is a quinolinyl or isoquinolinyl radical which is unsubstituted or substituted by $R^5$ and/or $R^6$, $R^3$ and $R^4$ are each, independently of one another, H, Hal, A, QA, OH or CN, $R^5$ and $R^6$ are each, independently of one another, H, CN, acyl, Hal, A, OA, OH, $CONH_2$, CONHA or $CONA_2$, $Het^1$ is a monocyclic or bicyclic, unsaturated heterocyclic ring system which is unsubstituted or monosubstituted or disubstituted by Hal, A, OA or OH and which contains one, two or three identical or different heteroatoms selected from nitrogen, oxygen and sulfur, A is alkyl having 1-6 carbon atoms, alk is alkylene having 2-6 carbon atoms, Hal is F, Cl, Br or I, or a physiologically acceptable salt or solvate thereof.

14. A compound of the formula I according to claim 13, wherein the solvate of a compound of formula I is a hydrate or alcoholate of a compound of formula I.

15. A compound of the formula I according to claim 13, wherein the solvate of a compound of formula I is a mono- or dihydrate or addition compound with methanol or ethanol of a compound of formula I.

16. A pharmaceutical composition comprising a compound of the formula I according to claim 1 or a physiologically acceptable salt thereof, and at least one solid, liquid or semi-liquid excipients or assistant.

* * * * *

UNITED STATES PATENT AND TRADEMARK OFFICE
CERTIFICATE OF CORRECTION

PATENT NO. : 7,329,749 B2  Page 1 of 1
APPLICATION NO. : 10/466487
DATED : February 12, 2008
INVENTOR(S) : Henning Boettcher It is certified that error appears in the above-identified patent and that said Letters Patent is hereby corrected as shown below:

Column 14, line 9 claim 10 reads "7-benz-9", should read -- 7-benz-2, --

Signed and Sealed this

Fifteenth Day of July, 2008

JON W. DUDAS
*Director of the United States Patent and Trademark Office*